United States Patent [19]
Vicenzi

[11] Patent Number: 5,969,157
[45] Date of Patent: Oct. 19, 1999

[54] PROCESS FOR THE SYNTHESIS OF BENZOTHIOPHENES

[75] Inventor: Jeffrey Thomas Vicenzi, Brownsburg, Ind.

[73] Assignee: Eli Lilly and Company, Indianapolis, Ind.

[21] Appl. No.: 08/972,783

[22] Filed: Nov. 18, 1997

Related U.S. Application Data

[60] Provisional application No. 60/031,181, Nov. 19, 1996.

[51] Int. Cl.$^6$ ................. C07D 333/52; C07D 409/00; C07D 405/00
[52] U.S. Cl. ................. 549/51; 546/202; 548/525; 540/596
[58] Field of Search ................. 549/51; 546/202; 548/525; 540/596

[56] References Cited

U.S. PATENT DOCUMENTS

| | | | |
|---|---|---|---|
| 4,075,227 | 2/1978 | Jones et al. | 549/51 |
| 4,133,814 | 1/1979 | Jones et al. | 544/146 |
| 4,233,333 | 11/1980 | Trummlitz et al. | 549/62 |
| 4,380,635 | 4/1983 | Peters | 546/202 |
| 4,418,068 | 11/1983 | Jones | 549/51 |
| 4,436,748 | 3/1984 | Ong et al. | 549/51 |
| 4,544,746 | 10/1985 | Holtje | 546/103 |
| 5,292,894 | 3/1994 | Ebel et al. | 549/52 |
| 5,472,962 | 12/1995 | Koizumi et al. | 549/51 |
| 5,512,684 | 4/1996 | Alt | 549/51 |
| 5,552,401 | 9/1996 | Cullinan et al. | 549/51 |
| 5,606,075 | 2/1997 | Hoard et al. | 549/51 |
| 5,606,076 | 2/1997 | Aikins et al. | 549/57 |
| 5,614,639 | 3/1997 | Hauser et al. | 549/57 |
| 5,792,870 | 8/1998 | Godfrey | 546/202 |

FOREIGN PATENT DOCUMENTS

| | | |
|---|---|---|
| 0062504 A1 | 10/1982 | European Pat. Off. . |
| 0556680 A1 | 2/1993 | European Pat. Off. . |
| 0691488 A1 | 1/1996 | European Pat. Off. . |

OTHER PUBLICATIONS

Guy, "Utilization of Polyphosphonic Acid in the Presence of a Co–solvent," *Synthesis*, 222–223, (Mar., 1985).

Ple,. et al., "Synthesis of Substituted Benzo[b] by Thiophene, [b] Acid–Catalyzed Cyclization of Thiophenyl Acctals and Ketone", *J. Heterocyclic Chem.*, 25, 1271–1272 (1988).

Kost et al., "Isomerization of 3–Substitutal Indoles, Benzo Furens, and Benzo[b] Thiophenes", Translated from *Zhurnal Organicheskoi Khimii*, vol. 6, No. 7, pp. 1503–1505 (Jul. 1970).

Merck Index, 1983, 10$^{th}$ Ed. Entry 7453.

*Primary Examiner*—Deborah C. Lambkin
*Attorney, Agent, or Firm*—Gilbert T. Voy

[57] ABSTRACT

The instant invention provides improved processes for preparing benzothiophenes utilizing methanesulfonic acid.

11 Claims, No Drawings

PROCESS FOR THE SYNTHESIS OF BENZOTHIOPHENES

BACKGROUND OF THE INVENTION

This application claims the benefit of U.S. Provisional Application Ser. No. 60/031,181 filed Nov. 19, 1996.

This invention relates to the field of pharmaceutical chemistry, and provides an advantageous process for preparing a group of benzothiophenes from dialkoxyacetophenones. The process provides the desired compounds in excellent yield on a large scale.

The preparation of benzothiophenes through a dialkoxy benzothiophene intermediate was previously described in U.S. Pat. No. 4,380,635, which teaches the intramolecular cyclization of a-(3-methoxyphenylthio)-4-methoxyacetophenone in the presence of polyphosphoric acid (PPA). Heating the acetophenone starting material in PPA at about 85° C. for about 1 hour provides an approximately 3:1 mixture of two isomers, 6-methoxy-2-(4-methoxyphenyl)benzo[b]thiophene and 4-methoxy-2-(4-methoxyphenyl)benzo[b]thiophene. However, when this reaction is conducted on a manufacturing scale, the isomeric benzothiophenes precipitate and produce a thick paste that cannot be stirred adequately in conventional manufacturing equipment.

Use of a solvent to alleviate the problem caused by a paste in a different reaction scheme has been attempted by Guy et al., *Synthesis*, 222 (1980). However, when this approach is applied to the instant scheme, the addition of a solvent results in incomplete cyclization of the starting acetophenone, incomplete rearrangement of 6-methoxy-3-(4-methoxyphenyl)benzo[b]thiophene, and dramatically increased reaction times.

Thus, there is a need for an improved process for the conversion of dialkoxyacetophenone derivatives to benzothiophenes with suitable yields and acceptable reaction times.

SUMMARY OF THE INVENTION

The present invention provides a process for the preparation of benzothiophenes utilizing methanesulfonic acid. This preparation relies on an intramolecular cyclization of a dialkoxyacetophenone derivative to yield a benzothiophene.

Thus, the invention provides a process for preparing a compound of formula Ib

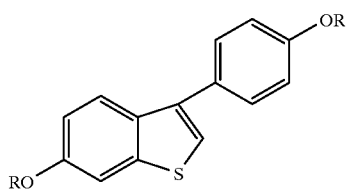

wherein the R groups are the same or different, and represent $C_1$–$C_6$ alkyl;

which includes cyclizing a compound of formula II

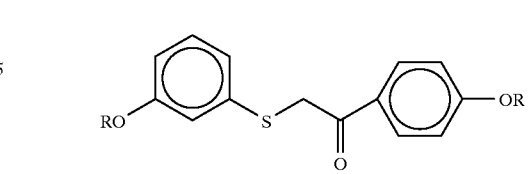

wherein the R groups are as defined above, in the presence of methanesulfonic acid.

DETAILED DESCRIPTION OF THE INVENTION

Benzothiophene is a key intermediate in the synthesis of raloxifene (a compound of formula III, wherein $R_1$ and $R_2$ combine to form 1-piperidinyl), which is a selective estrogen receptor modulator, or SERM. In addition to providing a process for the preparation of this intermediate, the present invention additionally provides a process for preparing a compound of formula III

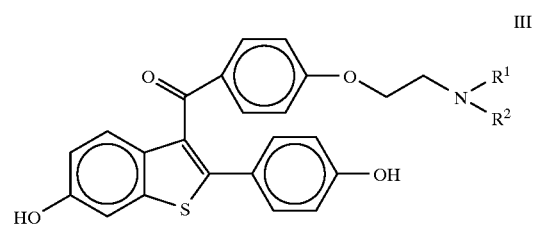

wherein:

$R_1$ and $R_2$ are independently $C_1$–$C_6$ alkyl, or combine to form, with the nitrogen to which they are attached, piperidinyl, pyrrolidinyl, methylpyrrolidinyl, dimethylpyrrolidinyl, or hexamethyleneimino, or the pharmaceutically acceptable salts or solvates thereof;

which includes cyclizing a compound of formula II

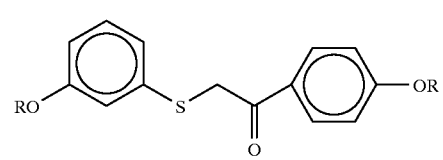

wherein the R groups are the same or different, and represent $C_1$–$C_6$ alkyl, in the presence of methanesulfonic acid.

Many of the starting materials and compounds prepared by the process of this invention are further provided in U.S. Pat. Nos. 4,133,814 and 4,380,635, the disclosures of which are herein incorporated by reference.

In this document, all temperatures will be stated in degrees Celsius. All amounts, ratios, concentrations, proportions and the like will be stated in weight units, unless otherwise stated, except for ratios of solvents, which are in volume units.

The term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, 2-methylpentyl, and the like. The term "$C_1$–$C_4$ alkyl" represents a straight or branched alkyl chain having from one to four carbon atoms, and includes methyl, ethyl, n-propyl, isopropyl, n-butyl, sec-butyl, i-butyl, and t-butyl.

The process for preparing compounds of formula I as provided by the instant invention is shown below in Scheme I:

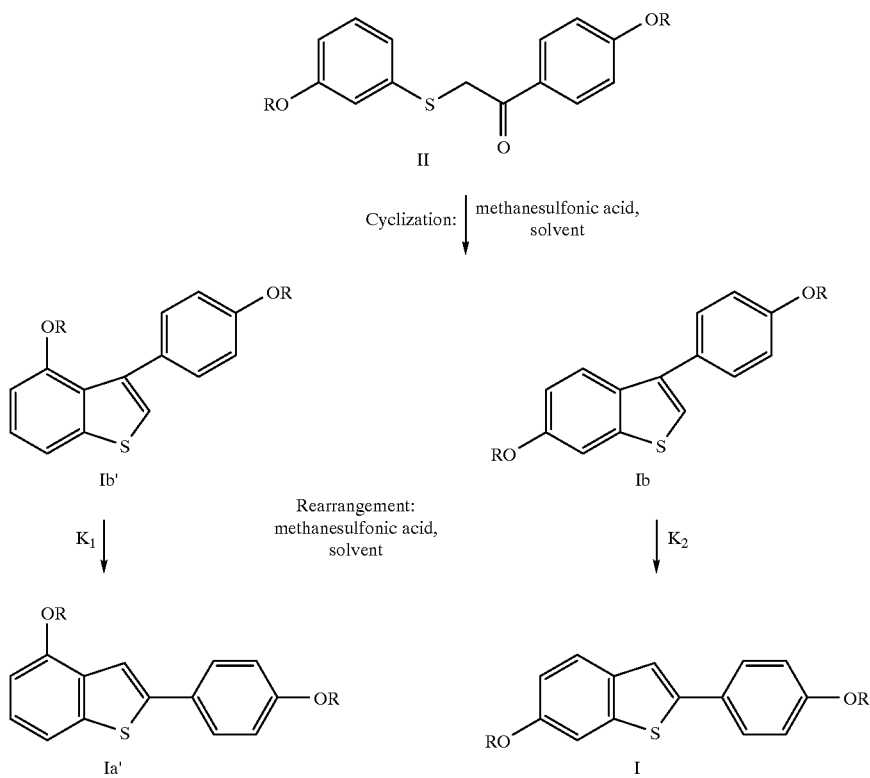

Scheme I

The overall reaction process comprises a first cyclization step and a subsequent rearrangement step. A compound of formula I is the desired product. The starting materials (compounds of formula II) for the processes of the present invention may be obtained by a number of routes, including those disclosed in U.S. Pat. Nos. 4,133,814 and 4,380,635.

Solvents including solvent mixtures and co-solvents employed in the practice of the present invention may affect the overall reaction, including reaction products and overall yield. Typically, the solvent of choice is a very weak base. The preferred solvent for the practice of the present invention is an aromatic solvent, with reasonable results obtained in both aliphatic and chlorinated solvents. Exemplary solvents include but are not limited to toluene, heptane, xylene, chlorobenzene, dimethoxyethane, and tetrachloroethylene. Preferred for the practice of the present invention is toluene.

The cyclization reaction in the first step occurs in the presence of methanesulfonic acid, and in general occurs approximately 50–100 times faster than the subsequent rearrangement reaction.

The cyclization reaction rate may be increased by increasing the amount of methanesulfonic acid employed in the reaction mixture. The reaction is typically run under reflux with the azeotropic removal of water.

According to the invention, the cyclization reaction is conducted at temperatures from about 50° C. to about 110° C., preferably from about 75° C. to 110° C., and most preferably from about 80 to 110° C.

The acetophenone starting material (a compound of formula II) is heated in the presence of methanesulfonic acid and toluene for at least 30 minutes, and preferably from about 60 to 300 minutes. As presently practiced, the acetophenone is cyclized and rearranged at about 90° C. for about 3–5 hours. The further addition of heptane at this time is optional, but may provide an enhanced reaction yield. After the addition of heptane, it is preferred to maintain the temperature at around 90° C.

Various desmethyl side products may form during both the cyclization and rearrangement reactions. The structures of 4 different desmethyl side products are provided in Scheme II below:

Scheme II

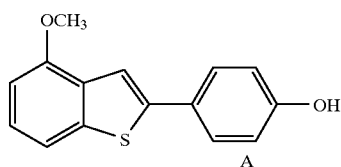

A

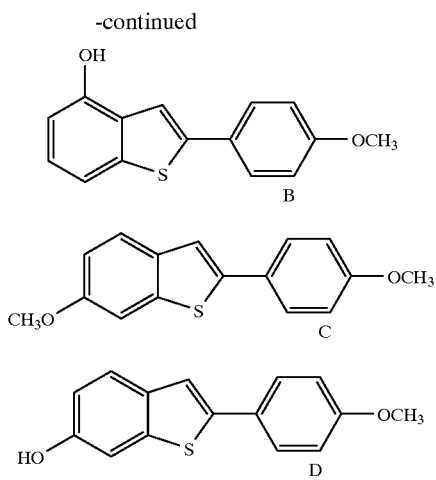

Isomers A and B are derived from a compound of formula Ia', while isomers C and D are derived from a compound of formula I. The ratio of isomers A:B:C:D in a typical reaction mixture was roughly 1:1:9:9. Isomer identity was generally confirmed by HPLC. The isomer ratio, and hence the ultimate yield, is determined by the kinetically-controlled cyclization reaction. Using methanesulfonic acid in toluene, a preferred isomer ratio of 75:25 to 80:20 (I/Ia') was obtained in the cyclization step, compared to an isomer ratio of 75:25 obtained when using polyphosphoric acid in the cyclization step. Further equilibration between ortho and para isomers during this process was not observed.

The rearrangement reaction is a thermodynamically controlled reaction. The equilibrium constants for said reaction are as follows: $K_1$ is >100, while $K_2$ is approximately 7–9. Using methanesulfonic acid and toluene/heptane as the solvent system, a compound of formula Ia precipitates as it forms in the reaction mixture, thereby driving the reaction to completion. The rearrangement of the undesired isomer, a compound of formula Ib', was 3–5 times faster than the rearrangement of the desired isomer, a compound of formula Ib.

Heptane is an additionally preferred solvent, which affects the crystallization of the benzothiophene products. This crystallization produces a reduction in the solubility, hence driving the equilibrium of the reaction. Heptane is best added to the reaction mixture prior to equilibrium.

A suitable solvent or solvent mixture may be further added to the reaction mixture at the end of the rearrangement reaction in order to quench the reaction. An example of a suitable solvent would include but not be limited to isopropanol (IPA), and the like. This solvent addition reduces the solubility of the product, as well as improves the purity of same.

The overall process may be operated as a "one-pot" synthesis, batchwise, semi-continuously, continuously, and the like. One skilled in the art would appreciate the differences between these modes of operation, including which reaction would be employed for a given purpose. For example, in semi-continuous or continuous operation the starting material and solvent are fed to a packed column of the solid acid resin. Recovery and isolation of excess solvent and product may be accomplished by distillation. Further, the reaction is optionally perfomed in the presence of an organic solvent which forms an azeotrope with water, and thus facilitates the removal of by-product by azeotropic distillation during the reaction process. Examples of such solvents which may be employed include aromatic hydrocarbons such as benzene, toluene, xylene, and the like.

The benzothiophene product may be isolated with a standard extractive workup by adding water, separating the layers, optionally extracting the aqueous layer again with the organic solvent, combining the organic layers, and concentrating the combined organic layers. When the starting material is the methoxy-derivative, the desired 6-alkoxy compound crystallizes in the concentrated solvent while the 4-alkoxy isomer remains in solution. The desired 6-alkoxy compound may be collected by filtration.

In a preferred cyclization process according to the invention, the starting material is a-(3-methoxyphenylthio)-4-methoxyacetophenone, which yields, upon workup after cyclization and rearrangement, 6-methoxy-2-(4-methoxyphenyl)benzo[b]thiophene. This material may subsequently be converted into a compound of formula III, such as for example, 6-hydroxy-2-(4-hydroxyphenyl)-3-[4-(2-aminoethoxy)benzoyl]benzo[b]thiophene. Conversion of 6-alkoxy-2-(4-alkoxyphenyl)benzo[b]thiophene to compounds of formula III may be accomplished according to the reactions as provided in U.S. Pat. No. 4,380,635.

Appropriate activating ester groups (R) are known in the art. Numerous reactions for the formation and removal of protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for nonregioselective removal of hydroxy protecting groups, particularly methyl, are known in the art. Compounds of formula III which have previously been protected at the 6- and 4'- position with methoxy may be selectively cleaved to generate compounds of formula III with a 4'-methoxy group. In general, the procedure for cleavage of a methoxy group on the 4' position involves the combination of a 6-, 4'-dimethoxy substrate with a demethylation reagent chosen from the group of boron tribromide, boron trichloride, or boron triiodide, or with $AlCl_3$ and various thiol reagents, such as EtSH. The reaction is conducted under an inert atmosphere such as nitrogen, with one or more moles of the reagent per mole of methoxy group to be cleaved.

Appropriate solvents for the deprotection reaction are those solvents or mixture of solvents which remain inert throughout the demethylation reaction. Halogenated solvents such as dichloromethane, 1,2-dichloroethane, and chloroform, or aromatic solvents such as benzene or toluene are preferred. The temperature employed in this reaction should be sufficient to effect completion of the demethylation reaction. However, it is advantageous to keep the temperature below 0° C. in order to maximize selectivity for cleavage of the 4'-methoxy group and avoid the formation of undesirable byproducts especially the product 6, 4'-dihydroxy analog arising from excessive demethylation. Under the preferred reaction conditions, a selectively dealkylated product will be formed after stirring the reaction for about 1 to 24 hours. A preferred variation involves the use of boron tribromide in the amount of approximately 1.5 moles with one mole of the 6-, 4'-dimethoxy substrate in dichloromethane under a nitrogen atmosphere at a temperature of −20° C. for 1 to 4 hours.

The compounds of formula III are very often administered in the form of acid addition salts. The salts are conveniently formed, as is usual in organic chemistry, by reacting the compound prepared according to this invention with a suitable acid. The salts are quickly formed in high yields at moderate temperatures, and often are prepared by merely isolating the compound from a suitable acidic wash as the final step of the synthesis. For example, salts may be formed with inorganic or organic acids.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The following compounds of formula III are provided as a further illustration of the overall process disclosed herein:

6-hydroxy-2-(4-hydroxyphenyl)-3-[4-(2-dimethylaminoethoxy)-benzoyl]benzo[b]thiophene;

3-(4-(2-ethoxymethylaminoethoxy)benzoyl]-6-hydroxy-2-(4-hydroxylphenyl)benzo[b]thiophene;

3-[4-(2-ethoxylisopropylaminoethoxy)benzoyl]-6-hydroxy-2-(4-hydroxyphenyl))benzo[b]thiophene;

3-(4-(2-dibutylaminoethoxy)benzoyl]-5-hydroxy-2-(4-hydroxyphenyl)benzo[b]thiophene;

3-[4-(2-(1-methylpropyl)methylaminoethoxy]-benzoyl]-6-hydroxy-2-(4-hydroxyphenyl)benzo[b]thiophene;

6-hydroxy-2-(4-hydroxyphenyl)-3-[4-[2-di(2-methylpropyl)aminoethoxy]benzoyl]benzo[b]thiophene;

6-hydroxy-2-(4-hydroxyphenyl)-3-[4-(2-pyrrolidinoethoxy)benzoyl]benzo[b]thiophene;

6-hydroxy-2-(4-hydroxyphenyl)-3-[4-(2-piperidinoethoxy)benzoyl]benzo[b]thiophene;

6-hydroxy-2-(4-hydroxyphenyl)-3-[4-(2-morpholinoethoxy)benzoyl]benzo[b]thiophene;

3-[4-(2-hexamethyleneiminoethoxy)benzoyl]-6-hydroxy-2-(4- hydroxyphenyl)benzo[b]thiophene.

The following Example is provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

All experiments were run under positive pressure of dry nitrogen. All solvents and reagents were used as obtained. The percentages are generally calculated on a weight (w/w) basis; except for high performance liquid chromatography (HPLC) solvents which are calculated on a volume (v/v) basis. Proton nuclear magnetic resonance ($^1$H NMR) spectra and $^{13}$C nuclear magnetic resonance spectra ($^{13}$C NMR) were obtained on a Bruker AC-300 FTNMR spectrometer at 300.135 MHz or a GE QE-300 spectrometer at 300.15 MHz. Silica-gel flash chromatography may be performed as described by Still et al. using Silica Gel 60 (230–400 mesh, E. Merck). Still et al., *J. Org. Chem.*, 43, 2923 (1978). Elemental analyses for carbon, hydrogen, and nitrogen were determined on a Control Equipment Corporation 440 Elemental Analyzer. Elemental analyses for sulfur were determined on a Brinkman Colorimetric Elemental Analyzer. Melting points were determined in open glass capillaries on a Gallenkamp hot air bath melting point apparatus or a Mettler FP62 Automatic instrument, and are uncorrected. Field desorption mass spectra (FDMS) were obtained using a Varian Instruments VG 70-SE or VG ZAB-3F mass spectrometer. High resolution free atom bombardment mass spectra (FABMS) were obtained using a Varian Instruments VG ZAB-2SE mass spectrometer.

The yields of 6-methoxy-2-(4-methoxyphenyl) benzo[b] thiophene may be determined by high performance liquid chromatography (HPLC) in comparison to an authentic sample of this compound prepared by published synthetic routes. See, for example, U.S. Pat. No. 4,133,814.

EXAMPLE 1

40 g a-(3-methoxyphenylthio)-4-methoxyacetophenone, 5 g methanesulfonic acid, and 120 ml Toluol (Drum Stock) was added to a 1 liter, 3 neck round bottom flask, equipped with a reflux condenser and a Dean Stark trap. The trap was either prefilled with toluene, or extra solvent was added to the reactor. The mixture was heated to reflux and stirred for 2 hours while azeotropically removing the water. This mixture was then cooled to 90° C. An additional 9 g methanesulfonic acid was added to the reaction mixture, which was stirred for 3–5 hours at 90° C. 56 mls of heptane (Drum Stock) was added over 5–20 minutes. The mixture was then stirred at 90° C. for 1 hour, then stirred at 80° C. for 3–4 hours. 98 mls of isopropanol (IPA) (Drum Stock) was added over 5–20 minutes, and then refluxed for 30 minutes at approximately 83° C. The mixture was then cooled to 0° C. at a rate no faster than 50° C. per hour. This was then stirred for at least 1 hour at 0° C., filtered, washed twice with 75 ml 70/30 (Toluol/IPA), and dried overnight at 60° C. under full vacuum. Yield=70%; 100% potency; 0.4% desmethyl.

I claim:

1. A process for preparing a compound of formula Ib

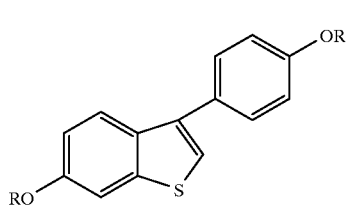

wherein the R groups are the same or different and represent $C_1$–$C_6$ alkyl, which comprises:

cyclizing a dialkoxy compound of formula II

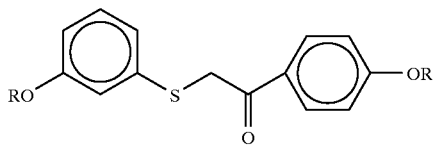

in the presence of methanesulfonic acid.

2. A process according to claim 1 which further comprises preparing a compound of formula I

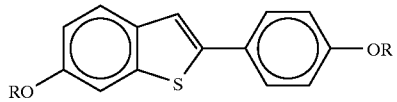

wherein the R groups are the same or different and represent $C_1$–$C_6$ alkyl, by rearranging a compound of formula Ib

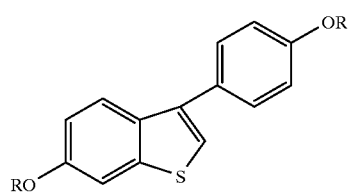

3. A process according to claim 1, wherein R is methyl.

4. A process according to claim 1, which further comprises the addition of toluene.

5. A process according to claim 4, which further comprises the addition of heptane.

6. A process according to claim 5, which further comprises the addition of isopropanol.

7. A process according to claim 1, wherein said cyclization is carried out at a temperature of from about 70° C. to about 90° C.

8. A process according to claim 1, wherein said process is carried out as a batch operation.

9. A process according to claim 1, wherein said process is carried out as a continuous operation.

10. In a process for preparing a compound of formula III

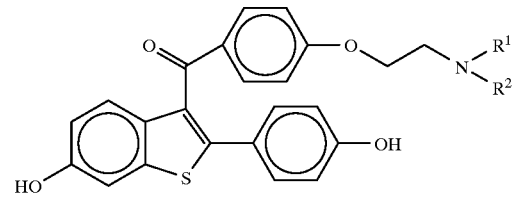

wherein:

$R_1$ and $R_2$ are independently $C_1$–$C_6$ alkyl, or combine to form, with the nitrogen to which they are attached, piperidinyl, pyrrolidinyl, methylpyrrolidinyl, dimethylpyrrolidinyl, or hexamethyleneimino, or the pharmaceutically acceptable salts or solvates thereof;

the improvement which comprises: cyclizing a compound of formula II

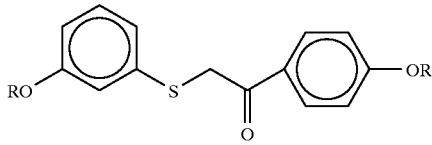

wherein the R groups are the same or different, and represent $C_1$–$C_6$ alkyl, in the presence of methanesulfonic acid.

11. A process according to claim 10, wherein R is methyl.

* * * * *